United States Patent
Worden

(10) Patent No.: US 7,112,342 B2
(45) Date of Patent: *Sep. 26, 2006

(54) ENRICHED PLATELET WOUND HEALANT

(75) Inventor: Charles E. Worden, Little Rock, AR (US)

(73) Assignee: Cytomedix, Inc., Deerfield, IL (US)

( * ) Notice: Subject to any disclaimer, the term of this patent is extended or adjusted under 35 U.S.C. 154(b) by 236 days.

This patent is subject to a terminal disclaimer.

(21) Appl. No.: 10/356,145

(22) Filed: Jan. 30, 2003

(65) Prior Publication Data

US 2004/0001816 A1 Jan. 1, 2004

Related U.S. Application Data

(60) Division of application No. 09/770,924, filed on Jan. 26, 2001, now Pat. No. 6,524,568, which is a continuation-in-part of application No. 09/424,523, filed on Nov. 23, 1999, now Pat. No. 6,303,112, which is a continuation-in-part of application No. PCT/US99/02981, filed on Feb. 13, 1999.

(60) Provisional application No. 60/097,897, filed on Aug. 26, 1998, provisional application No. 60/090,167, filed on Jun. 22, 1998.

(51) Int. Cl.
 A61K 35/14 (2006.01)
 C02N 5/00 (2006.01)

(52) U.S. Cl. .................... 424/532; 424/93.72

(58) Field of Classification Search ............... 424/532, 424/93.72, 724, 725, 738, 739
See application file for complete search history.

(56) References Cited

U.S. PATENT DOCUMENTS

| | | | |
|---|---|---|---|
| 1,593,814 A | 7/1926 | Vogel | |
| 4,298,598 A | 11/1981 | Schwarz et al. | |
| 4,485,096 A | 11/1984 | Bell | |
| 5,011,695 A | 4/1991 | Dichtelmuller et al. | 424/529 |
| 5,165,938 A | 11/1992 | Knighton | 424/532 |
| 5,178,883 A | 1/1993 | Knighton | 424/532 |
| 5,510,102 A | 4/1996 | Cochrum | 424/78.08 |
| 5,607,694 A | 3/1997 | Marx | |
| 6,303,112 B1 * | 10/2001 | Worden | 424/78.06 |

FOREIGN PATENT DOCUMENTS

| | | |
|---|---|---|
| EP | 0 493 985 A1 | 7/1992 |
| EP | 0 516 901 A1 | 12/1992 |
| EP | 0 637 450 A2 | 2/1995 |
| FR | 2 667 789 A1 | 4/1992 |
| GB | 2146 335 A | 4/1985 |
| WO | WO 86/03122 | 6/1986 |
| WO | WO 96/40174 | 12/1996 |
| WO | WO 98/55140 | 12/1998 |
| WO | WO 99/32135 | 7/1999 |
| WO | WO 99/66923 | 12/1999 |

OTHER PUBLICATIONS

The Merck Index, Merck & Co., Inc., 9th Ed., 1979, pp. 110-111.*
Appling, W. D., "Synergistic enhancement of type I and III collagen production in cultured fibroblasts by transforming growth factor-β and ascorbate", Federation of European Biochemical Societies (FEBS), vol. 250(2), 541-544, Jul. 1989.
Memorandum Opinion And Order, Cytomedix, Inc. v. Little Rock Foot Clinic, P.A., et al., Civil Action No. 02 C 4782, Judge James B. Zagel, N.D. Ill., Mar. 23, 2004, pp. 1-16.
Memorandum Opinion And Order, Cytomedix, Inc. v. Little Rock Foot Clinic, P.A., et al., Civil Action No. 02 C 4782, Judge James B. Zagel, U.S. Dist. Ct., N.D. Ill., Jul. 26, 2004, pp. 1-9.
Memorandum And Order, Harvest Technologies Corporation v. Cytomedix, Inc., Civil Action No. 02-12077-PBS, Judge Patti B. Saris, U.S. Dist. Ct., Dist. of Ma., Sep. 9,2004, pp. 1-25.
Post-Trial Supplementation Of The Court's Memorandum And Order Dated Sep. 9, 2004, Harvest Technologies Corporation v. Cytomedix, Inc., Civil Action No. 02-12077-PBS, Judge Patti B. Saris, U.S. Dist. Ct., Dist. of Ma., Jun. 14, 2005, pp. 1-2.
Expert Report Of Dr. Alan D. Michelson On Invalidity Of U.S. Patent No. 5,165,938, Harvest Technologies Corporation v. Cytomedix, Inc., Civil Action No. 02-12077-PBS, Judge Patti B. Saris, U.S. Dist. Ct., Dist. of Ma., Dec. 15, 2004, and Curriculum Vitae (Exhibit A).
Rosenthal, A. Ralph, et al., Use of a platelet-fibrinogen-thrombin mixture as a corneal adhesive: experiments with sutureless lamellar keratoplasty in the rabbit, Investigative Ophthalmology, vol. 14, No. 11, Nov. 1975, pp. 872-875, Exhibit D to Expert Reports Of Dr. Alan D. Michelson and Dr. Herbert Dardik.
Rosenthal, A. Ralph, et al., Use of Platelet-Fibrinogen-Thrombin Mixture to Seal Experimental Penetrating Corneal Wounds, Graefes Archiv Ophthalmologia, Apr. 6, 1978, vol. 207, pp. 111-115, Exhibit E to Expert Reports Of Dr. Alan D. Michelson and Dr. Herbert Dardik.
Pearl, Robert M., et al., Microvascular Anastomosis Using A Blood Product Sealant-Adhesive, Surgery: Gynecology & Obstetrics, Feb. 1977, vol. 144, pp. 227-231, Exhibit F to Expert Reports Of Dr. Alan D. Michelson and Dr. Herbert Dardik.
Schulte, Von Willi, Die Eigenblutfüllung: eine neue Methode zur Versorgung größerer Knochendefekte nach intraoralen Eingriffen, DZZ 15, 1960 Heft 12, pp. 910-912, Exhibit G to Expert Reports Of Dr. Alan D. Michelson and Dr. Herbert Dardik.
English Translation to Schulte, Von Willi, Autologous Blood (Venous) Filling, DZZ-15-1960, No. 12, pp. 910-914, Exhibit G to Expert Reports Of Dr. Alan D. Michelson and Dr. Herbert Dardik.
Schulte, Von W., Zentrifugiertes Eigenblut zur Füllung großer Knochendefekte—eine Modifikation der Eigenblutmethode, DZZ 24, 1969, Heft 10, pp. 854-857, Exhibit H to Expert Reports Of Dr. Alan D. Michelson and Dr. Herbert Dardik.

(Continued)

Primary Examiner—Jean C. Witz
(74) Attorney, Agent, or Firm—Fitch, Even, Tabin & Flannery

(57) ABSTRACT

An improved platelet gel wound healant, and methods of preparation and use thereof for healing wounds are disclosed. The improved wound healant comprises a therapeutically effective amount of activated growth factors and ascorbic acid with optional one or more additional antioxidant such as vitamin A and/or E, and optional one or more antibiotics.

12 Claims, 1 Drawing Sheet

OTHER PUBLICATIONS

Figure 1:
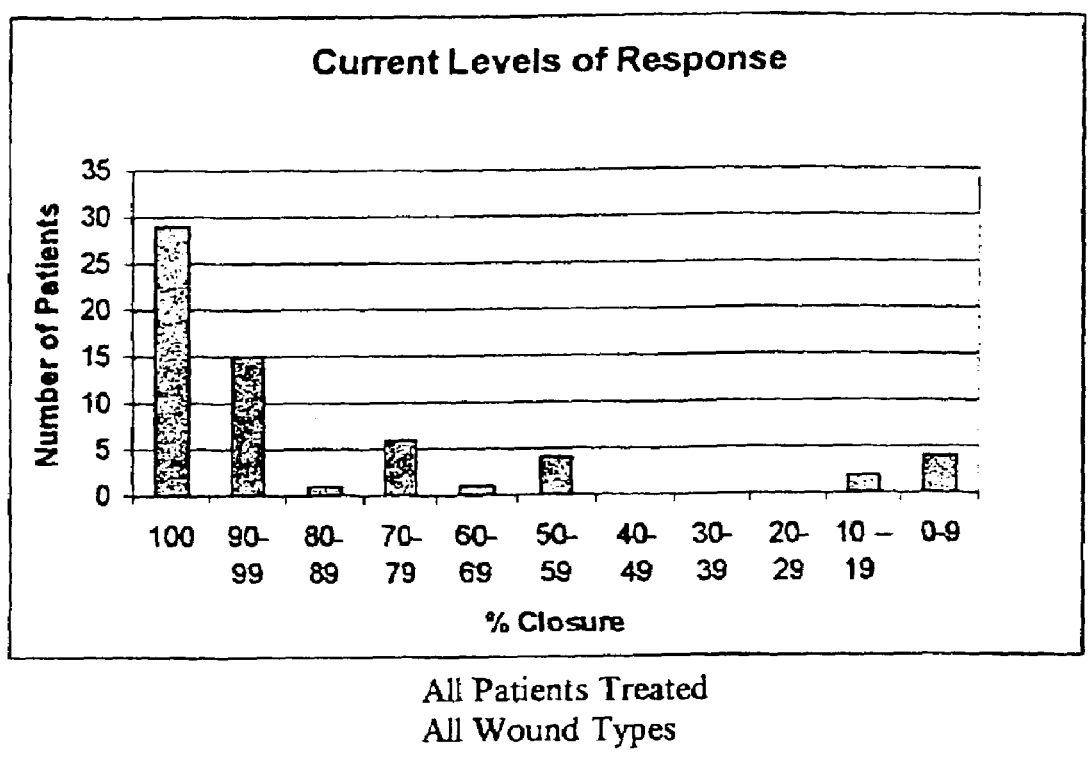

English Translation to Schulte, Von W., *Centrifuged Autologous Blood As Filling for Large Bone Defects (Modification of Whole Blood Method)*, DZZ-24-1969, No. 10, pp. 854-857, Exhibit H to Expert Reports Of Dr. Alan D. Michelson and Dr. Herbert Dardik.

Silverberg, Gerald D., et al., *A physiological sealant for cerebrospinal fluid leaks*, J. Neurosurg., vol. 46, Feb. 1977, pp. 215-219, Exhibit I to Expert Reports Of Dr. Alan D. Michelson and Dr. Herbert Dardik.

Knighton, David R., et al., *Role of Platelets and Fibrin in the Healing Sequence*, Annals of Surgery, vol. 196, Oct. 1982, No. 4, pp. 379-388, Exhibit K to Expert Reports Of Dr. Alan D. Michelson and Dr. Herbert Dardik.

Grotendorst, Gary, Ph.D., *Can Collagen Metabolism Be Controlled?* The Journal of Trauma, Sep. 1984, pp. S49-S54, Exhibit L to Expert Reports Of Dr. Alan D. Michelson and Dr. Herbert Dardik.

Grotendorst, Gary, et. al., *Molecular Mediators of Tissue Repair* , pp. 20-40, Exhibit M to Expert Reports Of Dr. Alan D. Michelson and Dr. Herbert Dardik.

Pohjanpelto, Pirkko, *Synergistic Effect of Thrombin and Platelet Extract on Growth of Human Fibroblasts* , Thrombosis Research, vol. 14, pp. 353-362, Exhibit N to Expert Reports Of Dr. Alan D. Michelson and Dr. Herbert Dardik.

Zucker-Franklin, D., et al., *Platelet Interaction with Cartilage—The Role of Proteoglycans in vitro and in vivo*, pp. 321-333, Exhibit O to Expert Reports Of Dr. Alan D. Michelson and Dr. Herbert Dardik.

Zucker-Franklin, D. et al., *Platelet Interaction with Modified Articular Cartilage*, The Journal of Clincial Investigation, vol. 59, Apr. 1977, pp. 641-651, Exhibit P to Expert Reports Of Dr. Alan D. Michelson and Dr. Herbert Dardik.

Bernstein, Lori R. et al., *Migration of Cultured Vascular Cells in Response to Plasma and Platelet-Derived Factors*, J. Cell. Sci., vol. 56, (1982), pp. 71-82, Exhibit Q to Expert Reports Of Dr. Alan D. Michelson and Dr. Herbert Dardik.

Kaplan, David R., et al., *Platelet a Granules Contain a Growth Factor for Fibroblasts*, Blood, vol. 532, No. 6, (Jun.), 1979, pp. 1043-1052, Exhibit R to Expert Reports Of Dr. Alan D. Michelson and Dr. Herbert Dardik.

Childs, Chris Bjornson, et al., *Serum contains a platelet-derived transforming growth factor*, Cell Biology, Proc. Natl. Acad. Sci. USA, vol. 79, Sep. 1982, pp. 5312-5316, Exhibit S to Expert Reports Of Dr. Alan D. Michelson and Dr. Herbert Dardik.

Ross, Russell, et al., *A Platelet-Dependent Serum Factor that Stimulates the Proliferation of Arterial Smooth Muscle Cells In Vitro*, Cell Biology, Proc. Natl. Acad. Sci. USA, vol. 71, No. 4, Apr. 1974, Exhibit T to Expert Reports Of Dr. Alan D. Michelson and Dr. Herbert Dardik.

Hunt, Thomas K., M.D., *Would Healing and Wound Infection*, 1980, Chapter 1, Ross, Russell, Inflammation, Cell Proliferation, and Connective Tissue Formation in Would Repair, pp. 1-10, Exhibit U to Expert Reports Of Dr. Alan D. Michelson and Dr. Herbert Dardik.

Hall, David A. et al, *International Review of Connective Tissue Research*, vol. 8, Oct. 1978, Beachey, Edwin H., et al, Collagen—Platelet Interaction, pp. 1-21, Exhibit V to Expert Reports Of Dr. Alan D. Michelson and Dr. Herbert Dardik.

Hunt, Thomas K. M.D., et al., *Fundamentals of Wound Management*, 1979, Chapter 1, Hunt, Thomas K. et al., Normal Repair, pp. 2-66, Exhibit W to Expert Reports Of Dr. Alan D. Michelson and Dr. Herbert Dardik.

Expert Report Of Dr. Herbert Dardik On Invalidity Of U.S. Patent No. 5,165,938, *Harvest Technologies Corporation v. Cytomedix , Inc.*, Civil Action No. 02-12077-PBS, Judge Patti B. Saris, U.S. Dist. Ct., Dist. of Ma., Dec. 15, 2004, and Curriculum Vitae (Exhibit A).

Rebuttal Expert Report Of Dr. Thomas K. Hunt, *Harvest Technologies Corporation v. Cytomedix, Inc.*,Civil Action No. 02-12077-PBS, Judge Patti B. Saris, U.S. Dist. Ct., Dist. of Ma., Dec. 15, 2004, Curriculum Vitae (Exhibit A), and Bibliography (Exhibit B).

Rebuttal Expert Report Of Dr. John H. Hartwig and Exhibits A-H, *Harvest Technologies Corporation v. Cytomedix, Inc.*, Civil Action No. 02-12077-PBS, Judge Patti B. Saris, U.S. Dist. Ct., Dist. of Ma., Feb. 25,2005.

Bejcek, Bruce E., et al., *Biosynthesis and Processing of the Platelet Derived Growth Factor Type a Receptor*, Biochemical and Biophysical Research Communications, vol. 196, No. 1, Oct. 15, 1993, pp. 69-78, Exhibit C to Rebuttal Expert Report Of Dr. John H. Hartwig.

Expert Report Of May S. Jacobson, PH.D. On Evaluation Of Growth Factor Release Using The Schulte Modified Protocol and Exhibits A-B, *Harvest Technologies Corporation v. Cytomedix, Inc.*, Civil Action No. 02-12077-PBS, Judge Patti B. Saris, U.S. Dist. Ct., Dist. of Ma., Dec. 15, 2004.

Expert Report Of Robert J. Mandle, PH.D. On Testing Of Invention Disclosed In U.S. Patent No. 4,314,380 and Exhibits A-B, *Harvest Technologies Corporation v. Cytomedix, Inc.*, Civil Action No. 02-12077-PBS, Judge Patti B. Saris, U.S. Dist. Ct., Dist. of Ma., Dec. 15, 2004.

Rebuttal Expert Report Of Dr. David R. Knighton, *Harvest Technologies Corporation v. Cytomedix, Inc.*, Civil Action No. 02-12077-PBS, Judge Patti B. Saris, U.S. Dist. Ct., Dist. of Ma., Feb. 25, 2005, Bibliography (Exhibit 2) and Curriculum Vitae (Exhibit 3).

Knighton, David R., M.D., et al., *Wound Repair: The Growth Factor Revolution*, Chronic Wound Care, Chpt, 46, pp. 431-445, Exhibit 1 to Rebuttal Expert Report Of Dr. David R. Knighton.

Grotendorst, PH.D., Gary, *Can Collagen Metabolism Be Controlled?*, The Journal of Trauma, Frontiers in Understanding Burn Injury, Sep. 1984, vol. 24, No. 9 Supplement, pp. S49-S54, cited in Rebuttal Expert Report Of Dr. David R. Knighton.

Ernst, Calvin B. et al., *A Prospective Randomized Trial of Autologous Platelet-Derived Wound Healing Factors for Treatment of Chronic Nonhealing Wounds: A Preliminary Report*, Letters to the Editors, Journal of Vascular Surgery, vol. 16, No. 1, Jul. 1992, pp. 124-128, cited in Rebuttal Expert Report Of Dr. David R. Knighton.

Lawrence, M.D., W. Thomas, et al., *The Reversal of an Adriamycin ® Induced Healing Impairment with Chemoattractants and Growth Factors*, Annals of Surgery, vol. 203, No. 2, Feb. 1986, pp. 142-147, cited in Rebuttal Expert Report Of Dr. David R. Knighton.

Sporn, Michael B. et al., *Polypeptide Transforming Growth Factors Isolated from Bovine Sources and Used for Wound Healing in vivo*, Science, vol. 219, Mar. 1983, cited in Rebuttal Expert Report Of Dr. David R. Knighton.

Senior, Robert M. et al., *Chemotactic Activity of Platelet Alpha Granule Proteins for Fibroblasts*, The Journal of Cell Biology, vol. 96, Feb. 1983, pp. 382-385, cited in Rebuttal Expert Report Of Dr. David R. Knighton.

Grotendorst, Gary R., et al., *Molecular Mediators of Tissue Repair*, pp. 20-40, cited in Rebuttal Expert Report Of Dr. David R. Knighton.

Michaeli, Dov, et al., *The Role of Platelets in Wound Healing: Demonstration of Angiogenic Activity*, pp. 380-394, cited in Rebuttal Expert Report Of Dr. David R. Knighton.

Davidson, Jeffrey M., et al., *Accelerated Wound Repair, Cell Proliferation, and Collagen Accumulation are Produced by a Cartilage-derived Growth Factor*, The Journal of Cell Biology, vol. 100, Apr. 1985, pp. 1219-1227, cited in Rebuttal Expert Of Dr. David R. Knighton.

Leitzel, Kim, et al., *Growth Factors and Wound Healing in the Hamster*, J. Dermatol. Surg. Oncol., 11:4, Jun. 1983, pp. 617-622, cited in Rebuttal Expert Report Of Dr. David R. Knighton.

Lawman, Michael J.P., et al., *Nerve Growth Factor Accelerates the Early Cellular Events Associated with Wound Healing*, Experimental and Molecular Pathology, vol. 43, No. 2, Oct. 1985, pp. 274-281, cited in Rebuttal Expert Report Of Dr. David R. Knighton.

Buckley, Anne, et al., *Sustained release of epidermal growth factor accelerates wound repair*, Proc. Natl. Acad. Sci. USA, vol. 82, No. 21, Nov. 1985, pp. 7340-7344, cited in Rebuttal Expert Report Of Dr. David R. Knighton.

Ross, Russell, et al., *Platelet-derived growth factor: its potential roles in wound healing, atherosclerosis, neoplasia, and growth development*, PDGF: Potential Roles in Biology, pp. 98-112, cited in Rebuttal Expert Report Of Dr. David R. Knighton.

Grotendorst, Gary R. et al., *Stimulation of Granulation Tissue Formulation by Platelet-derived Growth Factor in Normal and*

*Diabetic Rats*, J. Clin. Invest., vol. 76, No. 4, Oct. 1985, pp. 2323-2329, cited in Rebuttal Expert Report Of Dr. David R. Knighton.

Clark, Richard A.F., *Cutaneous tissue repair: Basic biologic considerations*, Journal of the American Academy of Dermatology, vol. 13, No. 5, Pt. 1, Nov. 1985, pp. 701-725, cited in Rebuttal Expert Report Of Dr. David R. Knighton.

Brown, Gregory L., et al., *Enhancement of Epidermal Regeneration By Biosynthetic Epidermal Growth Factor*, J. Exp. Med., vol. 163, May 1986, pp. 1319-1324, cited in Rebuttal Expert Report Of Dr. David R. Knighton.

Knighton, M.D., David R., et al., *Classification and Treatment of Chronic Nonhealing Wounds, Successful Treatment with Autologous Platelet-derived Wound Healing Factors (PDWHF)*, Annals of Surgery, vol. 204, No. 3, Sep. 1986, pp. 322-330, cited in Rebuttal Expert Report Of Dr. David R. Knighton.

Schultz, Gregory S., et al., *Epithelial Wound Healing Enhanced by Transforming Growth Factor—a and Vaccinia Growth Factor*, Science, vol. 235, No. 4786, pp. 350-352, cited in Rebuttal Expert Report Of Dr. David R. Knighton.

Cromack, Douglas T., et al., *Transformming Growth Factor β Levels in Rat wound Chambers*, Journal of Surgical Research, vol. 42, No. 6, Jun. 1987, pp. 622-628, cited in Rebuttal Expert Report Of Dr. David R. Knighton.

Carter, D.M., et al., *Clinical Experience With Crude Preparations of Growth Factors in Healing of Chronic Wounds in Human Subjects*, Growth Factors and Other Aspects of Wound Healing: Biological and Clinical Implications, 1988, pp. 303-317, cited in Rebuttal Expert Report Of Dr. David R. Knighton.

Lynch, Samuel E., et al., *Role of platelet-derived growth factor in wound healing: Synergistic effects with other growth factors*, Proc. Natl. Acad. Sci. USA, vol. 84, Nov. 1987, pp. 7696-7700, cited in Rebuttal Expert Report Of Dr. David R. Knighton.

McGee, Gregory S., et al., *Recombinant Basic Fibroblast Growth Factor Accelerates Wound Healing*, Journal of Surgical Research, vol. 45, 1988, pp. 145-153, cited in Rebuttal Expert Report Of Dr. David R. Knighton.

Chvapil, M.D., Milos, et al., *Lanolin and Epidermal Growth Factor in Healing of Partial-Thickness Pig Wounds*, JBCR, vol. 9, No. 3, May/Jun. 1988, pp. 279-284, cited in Rebuttal Expert Report Of Dr. David R. Knighton.

Brown, Gregory L., et al., *Enhancement of Wound Healing by Topical Treatment With Epidermal Growth Factor*, The New England Journal of Medicine, vol. 321, No. 2, Jul. 13, 1989, pp. 76-79, cited in Rebuttal Expert Report Of Dr. David R. Knighton.

Knighton, M.D. David R., et al., *Stimulation of Repair in Chronic, Nonhealing Cutaneous Ulcers Using Platelet-Derived Wound Healing Formula*, Surgery, Gynecology & Obstetrics, vol. 170, No. 1, Jan. 1990, pp. 56-60, cited in Rebuttal Expert Report Of Dr. David R. Knighton.

Doucette, Margaret M., et al., *Amputation Prevention in a High-Risk Population Through Comprehensive Wound-Healing Protocol*, Arch Phys Rehabil, vol. 70, Oct. 1989, pp. 780-785, cited in Rebuttal Expert Report Of Dr. David R. Knighton.

Knighton, M.D., David R., et al., *Wound Healing and Amputation in a High Risk Diabetic Population*, Wounds: A Compendium of Clinical Research and Practice, vol. 1, No. 2, Aug. 1989, pp. 107-114, cited in Rebuttal Expert Report Of Dr. David R. Knighton.

Fylling, Carelyn P., et al., *The Use of a Comprehensive Wound Care Protocol Including Topical Growth Factor Therapy in Treatment of Diabetic Neuropathic Ulcers*, Topical Growth Factor in Neuropathic Ulcers, pp. 567-578, cited in Rebuttal Expert Report Of Dr. David R. Knighton.

Atri, MS, MNAMS, Subhash Chandra, et al., *Use of homologous platelet factors in achieving total healing of recalcitrant skin ulcers*, Surgery, vol. 108, No. 3, pp. 508-512, cited in Rebuttal Expert Report Of Dr. David R. Knighton.

Steed, M.D., David L., et al., *Randomized Prospective Double-Blind Trial in Healing Chronic Diabetic Foot Ulcers*, Diabetes Care, vol. 15, No. 11, Nov. 1991, pp. 1598-1604, cited in Rebuttal Expert Report Of Dr. David R. Knighton.

Holloway, G. Allen, et al., *A randomized, controlled, multicenter, dose response trial of activated platelet supernatant, topical CT-102 in chronic, nonhealing diabetic wounds*, Wounds, vol. 5, No. 4, Jul./Aug. 1993, pp. 198-206, cited in Rebuttal Expert Report Of Dr. David R. Knighton.

Spence, R.K., et al. *Activated platelet supernatant, topical (APST) in the treatment of chronic venous stasis ulceration*, Abstract, American Venous Forum, Maui, Hawaii, Feb. 1994, cited in Rebuttal Expert Report Of Dr. David R. Knighton.

Keyser, M.D., John E., *Diabetic Wound Healing and Limb Salvage in an Outpatient Wound Care Program*, Southern Medical Journal, vol. 86, No. 3, Mar. 1993, pp. 311-317, cited in Rebuttal Expert Report Of Dr. David R. Knighton.

Glover, John L., et al., *A 4-Year Outcome-Based Retrospective Study of Wound Healing and Limb Salvage in Patients with Chronic Wounds*, Advances in Wound Care, vol. 10, No. 1, Jan./Feb. 1997, pp. 33-38, cited in Rebuttal Expert Report Of Dr. David R. Knighton.

Bentkover, PH.D., Judith D., et al., *Economic Evaluation of Alternative Methods of Treatment for Diabetic Foot Ulcer Patients: Cost-Effectiveness of Platelet Releasate and Wound Care Clinics*, Wounds, vol. 5, No. 4, Jul./Aug. 1993, pp. 207-215, cited in Rebuttal Expert Report Of Dr. David R. Knighton.

Duff, R., et al., *The correlation of chronic wound healing to growth factor levels in platelet extracts*, Correlation Studies, Correlate Wound Healing With Concentrations of Growth Factors, 3rd International Symposium on Tissue Repair, Miami, FL, Jan. 1990, cited in to Rebuttal Expert Report Of Dr. David R. Knighton.

* cited by examiner

All Patients Treated
All Wound Types 46.8% of the patients had 100% closure
Mean time to closure 8.74 weeks
Mean number of treatments 2.24
N= 62

ENRICHED PLATELET WOUND HEALANT

CROSS-REFERENCE

This is a divisional of U.S. patent application Ser. No. 09/770,924, filed Jan. 26, 2001; now U.S. Pat. No. 6,524,568 which is a continuation-in-part of U.S. patent application Ser. No. 09/424,523, filed Nov. 23, 1999 now U.S. Pat. No. 6,303,112; which is a continuation-in-part of PCT/US99/02981 filed Feb. 13, 1999; which claims benefit of Provisional Application Ser. No. 60/090,167, filed Jun. 22, 1998; and claims benefit of Provisional Application Ser. No. 60/097,897, filed Aug. 26, 1998; the entire contents of which are incorporated by reference.

FIELD OF THE INVENTION

The present invention relates to improved platelet enriched compositions for wound treatment and methods of making and use thereof.

BACKGROUND OF THE INVENTION

There have been many different substances and methods developed in the past for treating wounds, depending upon the type and location and severity of the wound. A wound is generally defined as an injury to an area of the body of a human or animal. Although injury to the surface of the skin is the most well known type of wound, the surfaces of internal organs may also be wounded, such as during surgery, rupture of the spleen or liver, or resulting from traumatic blows to the body surface in the vicinity of an internal organ.

Medical practice characterizes wounds as chronic or acute, according to the persistence and severity of the wound. A chronic wound is one that is prolonged or lingering, rather than promptly healed. An acute wound is one that occurs relatively quickly, and heals relatively quickly as well. Tissue wounds may have a wide spectrum of manifestations, as small as merely an abnormal microscopic tear or fissure in tissue (or a surface thereof), or as large as the abrasion or ablation of the skin covering a substantial portion of the body, such as in a burn victim. Acute wounds covering a large or movable surface are usually the most difficult to guard from infection, and to heal.

Blood and bodily fluids include various substances that affect wound healing. The blood is the primary medium for delivering healing agents to the wound site, and for transporting foreign or harmful substances away from the wound. Whole blood is primarily comprised of three main types of cells suspended in a protein rich solution known as plasma. The three main cell types in whole blood are erythrocytes (a.k.a. red blood cells), leukocytes (a.k.a. white blood cells) and thrombocytes (a.k.a. platelets). The red blood cells are the iron-containing cells that facilitate the transport and transfer of oxygen to body tissue, and the removal of carbon dioxide. The white blood cells perform a variety of functions such as phagocytosis of foreign bodies and production of antibodies, and are primarily responsible for fighting infection and foreign substances within the blood or wound site. Platelets perform many functions such as plugging leaks in blood vessels and helping begin the process leading to the formation of a blood clot; platelets contain substances known as growth factors that facilitate the formation of new tissue.

Although there are several methods for separating whole blood into its various components, one of the most convenient and expeditious methods is accomplished by differentially centrifuging blood or some of its components (i.e., apheresis). Using apheresis, the red and white blood cells and plasma may be separated out and returned to the donor's or patient's body, leaving the sequestered platelets in essentially concentrated form for use in wound healing techniques. From blood extracted from a patient, the platelets may thus be obtained and activated for use on the same patient; methods of using a patient's own blood are called "autologous" or "autogenic" donor methods. Methods using blood donated by one or more third parties for use by a patient are called "homologous" or "heterologous" donor methods, or collectively called "allogenic" methods.

One of the proteins suspended in plasma is fibrinogen, which reacts with substances released into (or attracted by) wound sites to produce sticky strands of fibrin. Such reactions result in the cross linking of the fibrin strands to form a mesh that holds and supports the deposit or growth of other tissue materials at the wound site.

The wound healing process is generally considered to occur in several stages, generally known as the healing cascade. After tissue injury, platelets are among the first cells to appear in the vicinity of the wound. Activation of a platelet by an agonist such as thrombin, or other agonists such as those listed elsewhere herein, leads to the release of granule material from within the platelet. Such granulation activation results in the release of proteins known as growth factors, primarily concentrated in the alpha granules of platelets. These released growth factors stimulate the formation of new tissue; when applied to wounds, growth factors have been known to increase the rate of collagen laydown, vascular ingrowth, fibroblast proliferation and overall healing. The release of a protein known as platelet-derived growth factor (PDGF) is a chemotactic signal for monocytes, neutrophils and fibroblasts which then move into the wound, to begin the inflammatory stage of the healing process. During this time, monocytes secrete a number of factors including PDGF and transforming growth factor-$\beta 1$ (also found in platelets), which recruits and activates fibroblasts, to begin the repair stage of the healing process. Subsequently, wound healing continues through the process of collagen remodeling within the wound.

Based upon the foregoing general scientific principles, already known in the field are wound sealants made from biological materials obtained primarily from tissue other than blood platelets. An example is wound sealants such as "fibrin glue," which often are essentially a mixture of co-coagulants (thrombin and calcium), concentrated fibrinogen and other coagulation proteins. In most applications, the primary roles of fibrin glue are to seal wound surfaces to prevent loss of blood and other body fluids after surgery, and to provide adhesion between adjacent tissue surfaces. These products form a hard, cast-like covering over the area to be sealed, and tend to be non-yielding to limb movement.

The production of fibrin glue often requires obtaining fibrinogen from blood through a process known as cryoprecipitation, including both freeze-thaw cycles and relatively lengthy centrifugation of plasma in controlled environments, to concentrate the fibrinogen in sufficiently for use; the precipitant thus obtained is frozen to $-20°$ to $-30°$ centigrade before storage. These requirements make such materials unsuitable for application during the course of surgery, especially emergency surgery without an hour or more lead time. Moreover, to the extent this process depends upon the use of autologous biological materials, using this process shortly before or during surgery may result in the loss of crucial bodily fluids during a time when the patient's body is badly in need of such fluids. By contrast, substantially larger amounts of concentrated platelets can be more conveniently obtained within a matter of minutes from more recent methods of differential blood centrifugation not requiring freezing and without significant loss of bodily fluids.

While there has been much research concerning fibrin glue, this material belongs to a separate field from the present invention, primarily because fibrin glues typically contain cryoprecipitated proteins without platelets. The use of fibrin glue is discussed extensively in the scientific literature; for example, see the references cited in U.S. Pat. No. 5,585,007 issued to Antanavich et. al. on Dec. 17, 1996.

Wound treatment compositions derived from platelet enriched concentrates are known and possess certain advantages over materials without platelets such as fibrin glue. One reason is that natural wound healing agents are released by the platelets. Further, the concentration of platelets likewise allows for a concentrated amount of wound healing factors. Additionally, to the extent that the wound healing composition is made from the biological materials of the patient, the risks associated with heterologous donors (such as disease, immunologic reactions, or the like) are eliminated. Representative examples of platelet derived wound treatment compositions are described for instance in Hood U.S. Pat. No. 5,733,545; Knighton U.S. Pat. No. 5,165,938; and Gordiner U.S. Pat. No. 5,599,558.

Platelet concentrates are typically isolated by the process of differential centrifugation which essentially allows separating the patient's own blood into at least three different components: packed erythrocytes (red blood cells), plasma and platelet concentrate. Platelet concentrate can be combined with a solution of either sodium or calcium mixed with thrombin ("calcified thrombin"), which instantaneously form a composition of activated platelets that, when made with the necessary viscosity, can be utilized as a wound sealant. The chemical reactions and cascades that normally occur when thrombin is added to the concentrated platelets are indeed complex. See, for instance, Reeder, et. al., in *Proceedings of the American Academy of Cardiovascular Perfusion*, Vol. 14, January 1993. Such wound sealants typically set up into a hard mass covering the application site, thereby sealing the site against further blood loss and external contaminants.

There are a number of disadvantages associated with conventional wound compositions derived from platelet concentrates. For instance, activation of platelets leads to instantaneous hardening of the material and thus requires the physician to both activate and apply the platelet composition to the wound site within seconds of activation. Also, certain platelet compositions must be applied to the wound site on a daily basis and thus require regular blood withdrawal from the patient. The presence of a hardened mass at the wound site is undesirable because it impedes oxygen transport into the wound which is necessary for tissue repair. It may also create a favorable environment for the growth of pathogenic anerobic bacteria.

Accordingly, an improved platelet enriched wound treatment composition which avoids or diminishes the problems associated with typical platelet enriched wound compositions would be desirable.

SUMMARY OF THE INVENTION

The present invention relates to an improved enriched platelet composition for wound treatment, a method of making and use thereof. The composition comprises platelets and an effective amount of an anti-oxidant, preferably ascorbic acid (vitamin C) so as to delay or prolong the activated gelation period to allow the practitioner sufficient time to apply the composition in liquid form to the wound site and to prevent the material from forming a hard seal. Optional antibiotics may be included in the improved composition to prevent infections at the wound site. The presence of the anti-oxidant, including vitamins and non-vitamin anti-oxidants, and other healing promotion materials that do not detract from, substantially interfere with, or even destroy the different thrombin activation reactions. The inventive platelet gels containing ascorbic acid retain a stable soft gel-like consistency during and after topical application at the wound site and avoid the requirement for daily reapplication.

While the inventive composition is preferably used for topical application to the exterior surface of the chronic wounds such as ulcers of the feet of diabetics, the composition may be applied to facilitate the healing of other wounds such as acute wounds such as burns. However, the composition of matter and the methods described herein are not limited solely to topical application.

The inventive composition increases the amount of growth factors in the wound, and thereby facilitates the promotion of the healing rate. This may be especially important in "wounded" patients, especially those with chronic wounds who may lack sufficient circulation to facilitate the healing cascade. The invention described herein also facilitates the covering of the wound area with a substance that prevents or helps to reduce infection caused by most bacteria; and to the extent that the wound treatment material is made from autologous blood or similar biological materials, the invention described herein reduces the risks associated with the use of the treatment materials made from biological materials obtained from one or more third parties. An autologous product avoids some of the common problems associated with the use of biological materials from third parties, such as (for example) screening to assure that the donor was biologically or immunologically compatible with the patient, and otherwise free of hepatitis, HIV and the like.

In most general terms, the invention described herein expands the uses for concentrated platelet materials, especially those in gel form, by improving the speed and convenience of making the composition; the invention described herein also improves the performance of the concentrated platelet composition, by making it more useable for applications over longer periods of time, and by enhancing the wound healing and infection fighting properties. For autologous platelet gel to be more useful, the gelatinous state must be capable of remaining stable for a reasonable period of time. One aspect of the present invention is to add an anti-oxidant to the platelet gel, such as ascorbic acid.

Another aspect of the present invention involves adding one or more antibiotic substance at one or more times during the processing period so that the resulting concentrated platelet composition contains either one or a variety of the antibiotics. The use of an antibiotic in concentrated platelet compositions that enhances the complex healing cascade is indeed novel. The invention disclosed herein involves adding such substances in a manner that does not detract from, substantially interfere with, or even destroy these different reactions, pH balances and potency.

Another aspect of the present invention involves adding one or more vitamins, in addition to ascorbic acid (vitamin C) to the concentrated platelet gel. Vitamins are known to have wound healing and anti-oxidant properties. Representative examples of suitable, but none limiting, vitamins include vitamin E, vitamin A and other retinoids.

In yet another aspect of the invention, non-vitamin anti-oxidants may be included in the concentrated platelet gel. Non-limiting representative examples of such anti-oxidants include p-carotene.

The method of making the invention in gel form described herein includes admixing at least one of the described additives with the plasma-poor concentrated platelets, a sufficient time before the addition of calcified thrombin (or other preferably-calcified agonist) to allow the desired dispersion of such additive(s) in such composition before gelation prevents further dispersion.

DETAILED DESCRIPTION OF THE FIGURES

FIG. 1 is an illustration summarizing the levels of response for all 62 patients with various wound types following treatment with the gel coagulum of the invention as described in Example 4. The results show that 46.8% of all patients had 100% closure after receiving, on average, 2.24 treatments over an averaged time duration of 8.74 weeks.

DETAILED DESCRIPTION OF THE INVENTION

Before the present invention is described in detail, it is to be understood that the invention is not limited to the particular configurations, process and materials expressly disclosed herein; the invention includes those that are implicit or inherent in the disclosures set forth herein, and all legal equivalents of an element(s) or limitation(s) thereof. As an example, the biological materials specified herein may originate from a patient to be treated, from a single third party, or from a plurality of third parties; moreover, said third parties may be of the same species as the patient, or of another species, so long as the wound treatment material derived from such biological materials is biocompatible with the patient. As another example, when the invention calls for a particular substance, it is sufficient to use any form of that substance having the characteristic(s) needed to satisfy the stated need; for instance, unless the context indicates otherwise, a need for growth factors may be satisfied by providing isolated growth factors or those that are included in platelets or other types of cells, and/or combinations thereof. Similarly, the process deployed to obtain the growth factors may be any process that satisfactorily does so, regardless of whether it includes centrifugation.

It is also to be understood that the terminology used herein is not intended to be limiting, since the scope of the present invention will be limited only by the claims and equivalents thereof. Also, as used herein, the singular forms include the plurals, and vice versa, unless the context indicates otherwise.

For the sake of simplicity and to give the claims of this patent application the broadest interpretation and construction possible, the following definitions will apply:

(a) The phrase blood collecting or blood extraction (or similar phrase) includes techniques, materials and apparatus known in the field, such as (for example) inclusion of anticoagulation materials, the use of blood drawing and infusion apparatus.

(b) The phrase growth factor means any material(s) promoting growth of a tissue.

(c) The term thrombin may include calcified thrombin, in particular, about 5,000 units of thrombin per 5 ml of 10% of aqueous calcium chloride solution; it may include calcified bovine thrombin as well as autologous thrombin, allogeneic thrombin or recombinant human thrombin.

(c) The term viscosity means those characteristics of the specified material(s) determining the degree of gelation, such as (for example) the firmness or hardness of the material, or the degree to which the material resists flowing like a fluid.

(d) The term therapeutically effective amount means the amount or amounts of the constituent elements or combination thereof necessary-to enhance wound healing such as, for example, the reduction in the volume or surface area of a wound, the increase in the amount of granulation tissue or other biological material facilitating collagen laydown, vascular ingrowth, fibroblast proliferation or overall healing; all of the versions of the invention described herein are assumed to have the therapeutically effect amount(s) of constituent substances, or combinations thereof.

(f) The term anti-oxidant refers to any material(s) having anti-oxidant properties. Anti-oxidant would include, without limitation, vitamins such as vitamins A and E and non-vitamins such as—carotene.

Also for the sake of simplicity, the conjunctive "and" may also be taken to include the disjunctive "or," and vice versa, whenever necessary to give the claims of this patent application the broadest interpretation and construction possible. Likewise, when the plural form is used it may be taken to include the singular form and vice versa.

In most general terms, the invention includes a wound healant composition comprising activated growth factors and ascorbic acid. In the prevalent version of the invention, said growth factors are included within platelets. The body produces many substances generally known as growth factors, and these growth factors are contemplated for use in the present invention. The preferred growth factors for use in the present invention are selected from the group consisting of platelet-derived growth factor (PDGF), platelet-derived angiogenesis factor (PDAF), vascular endotheial growth factor (VEGF), platelet-derived epidermal growth factor (PDEGF), platelet factor 4 (PF-4), transforming growth factor β (TGF-β), acidic fibroblast growth factor (FGF-A), basic fibroblast growth factor (FGF-B), transforming growth factor a (TGF-A), insulin-like growth factors 1 and 2 (IGF-1 and IGF-2), β thromboglobulin-related proteins (BTG), thrombospondin (TSP), fibronectin, von Wallinbrand's factor (vWF), fibropeptide A, fibrinogen, albumin, plasminogen activator inhibitor 1 (PAI-1), osteonectin, regulated upon activation normal T cell expressed and presumably secreted (RANTES), gro-α, vitronectin, fibrin D-dimer, factor V, antithrombin ID, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL-1), Keratinocyte Growth Factor-2 (KGF-2) and combinations thereof. One of the important characteristics common to each substance, supporting the inclusion of each in this particular group, is that each such substance is known or believed to enhance cell or tissue growth. Moreover, said substances, or various combinations thereof, are known or believed to function together in an unexpected synergistic manner to promote wound healing. Suitable, non-limiting, anti-oxidants useful in the invention include but are not limited to vitamins such as vitamin C (ascorbic acid), vitamin E, vitamin A and other retinoids; and the carotenes such as β-carotene. In practicing this invention, ascorbic acid as anti-oxidant is particularly preferred.

The presence of ascorbic acid in the concentrated platelet gel provides a number of surprising and beneficial effects. Ascorbic acid delays or prolongs the activated platelet gelation period to allow the practitioner sufficient time to readily apply the gel composition topically to the wound site and to prevent the applied material from forming an undesirable hard seal. The general amount of ascorbic acid that may be used in preparing the inventive composition is sufficient to enhance the preservation of the soft gelatinous state of the final wound healing composition. The amount of ascorbic acid generally ranges between about 10 mgs and about 100 mgs, preferably ranging between about 20 mgs and about 65 mgs, per ml of platelet concentrate. Ascorbic acid is available as Cenolate® ascorbic acid injection USP (500 mg/ml, pH 5.5–7.0; Abbott Laboratories, North Chicago, Ill., USA). This is a solution of sodium ascorbate that is prepared from ascorbic acid with sodium bicarbonate in water for injection.

The platelets are separated from the red blood cells and white blood cells of whole blood, primarily through differential centrifugation, although any suitable method for separating platelets from whole blood may be employed in practicing this invention. The overall composition of the invention disclosed herein may contain incidental amounts of white blood cells, due to the fact that the platelets are rarely totally isolated from the other blood components. It is believed that the present invention contains only minimal or trace amounts of white blood cells; it is believed that the white blood cell count of the present invention typically will be below about 3 times $10^7$ cell/ml. The bioactive material in the invention is almost exclusively from platelets. The range of the mean platelet volume of the platelets being sequestered is in the range of about 6.6 to 8.4 femtoliters, with an average of about 7.7 femtoliters; this may indicate that the platelets being sequestered are relatively larger or younger than the overall population of platelets.

Activation of growth factors may occur in a variety of manners, by a variety of substances known as activators or agonists. In the invention described herein, said activation results from the inclusion of an activator or agonist selected from the group consisting of thrombin, collagen, serotonin, adenosine diphosphate (ADP) and acetylcholine (ACH), and combinations thereof. In a particular and preferred version of the invention, said growth factors are included within concentrated platelets, and said activation results from the inclusion of thrombin. One of the important characteristics common to each substance, supporting the inclusion of each in this particular group, is that each such substance is known or believed to enhance cell or tissue growth in addition to the ability to activate platelets. Moreover, said substances, or various combinations thereof, are known or believed to function together in an unexpected synergistic manner to promote wound healing.

The activator or agonist added to the platelet concentrate is in an amount sufficient to facilitate the formation of the coagulum (gel) having a predetermined viscosity while sufficiently activating growth factors present in the composition. In the preferred case where thrombin is employed as the activator to produce a final soft gel wound composition in a soft gel form, the amount of thrombin generally ranges between about 100 U and about 10,000 U, preferably about 900 U and about 1100 U, most preferably about 1000 Upper 8 cc of platelet concentrate. Thrombin is available as Thombogen® thrombin, topical USP (bovine origin) in vials containing 5000 units thrombin (Johnson & Johnson Medical Inc., Arlington, Tex., USA).

Thrombin activation requires the presence of certain cofactors such as sodium or calcium. In practicing this invention, thrombin activation preferably occurs in the presence of calcium ions. Calcium ions are generally added to the platelet concentrate as a salt solution to provide a final concentration generally ranging between about 0.1 mg/ml and about 10 mg/ml, preferably 1 mg/8 cc of platelet concentrate. Suitable calcium salts include, without limitation, $CaCO_3$, and $CaSO_4$. A preferred calcium salt for use in the invention is $CaCl_2$. $CaCl_2$ is available as calcium chloride injection, USP 10% (American Regent Laboratories, Inc., Shirley, N.Y., USA).

The invention is not limited to autologous biological materials, such as collection of concentrated platelets from the wounded's own biological material. The invention encompasses the use of biological materials obtained from one or more third parties, that need not be of the same species as the patient whose wound is being treated with the wound healant composition described herein unless bioincompatibility would result from the use of such third party biological materials.

In one general version of the invention, the wound healant composition includes concentrated platelets, thrombin and ascorbic acid. Ascorbic acid is known to have preservative properties, unless it is broken down such as occurs after exposure to sunlight or another source of ultraviolet (UV) light rays. However, most versions of the invention described herein are covered by bandages or otherwise shielded from UV rays almost immediately after application to the wound site.

Since the admixture of thrombin or other agonists will activate growth factors, the thrombin (or other agonists/activators) should usually be the last substance to be mixed immediately before it is desired that the gelatinous state be set up.

Another version of the invention includes the inclusion of at least one other antioxidant vitamin, such as vitamin E, vitamin A and other retinoids in the admixture, in addition to or in substitution of the ascorbic acid Although the wound healant composition could include a combination of one or more vitamins, one version of the invention merely includes vitamin A in addition to or in substitution of the ascorbic acid. Vitamin A has been known to counteract a side effect of some treatments using steroids, namely, the depressed reactivity of the body immune system to stimuli. Furthermore, vitamin A is known or believed to inhibit or decrease the bioactivity of manganese, magnesium and copper in the cellular and interstitial environment; said elements are known or believed to be active or instrumental in the laying down of keloids and scar tissue. (See, "Effects of Pantothenic Acid and Ascorbic Acid Supplementation of Human Skin Wound Healing Process" by Vaxman et. al., *Eur. Surg. Res.* 1995, 28:4, 158–166.) The versions of the invention described herein containing vitamin A accordingly are believed to promote healing without as much scarring or keloid formation. In another version, vitamin E, known to facilitate healing, may be used. In any event, the vitamins disclosed herein (or combination thereof) appear to enhance wound healing in an unexpectedly synergistic manner in addition to their roles in gel formation. The general amount of vitamin that may be used in preparing the inventive composition is one that is sufficient to enhance the preservation of the soft gelatinous state of the final wound healing composition.

Since many wound sites are either already infected with bacteria or are susceptible to such infection, it is desirable that a wound healant composition be capable of either killing bacteria or preventing the mobility or reproduction of bacteria. The invention described herein includes a wound healant composition comprising concentrated platelets, thrombin and at least one antibiotic. In particular, the invention includes a wound healant wherein said antibiotic is bacteriocidal to at least the *Pseudomonas* and *Klebsella* genera of bacteria, which are prevalent at wound sites and difficult to guard against. Alternatively, said antibiotic is selected from the group consisting of a neosporin, vancomycin and gentamycin, and combinations thereof. One of the important characteristics common to each substance, supporting the inclusion of each in this particular group, is that each such substance is known to kill said bacteria.

As indicated above, the invention may include a wound healant composition comprising concentrated platelets, thrombin, ascorbic acid, at least one retinoid and at least one antibiotic bacteriocidal to the *Pseudomonas* and *Klebsella* genera of bacteria.

Aside from the wound healant substance to be applied to wound sites, the invention further includes a method of making a healant composition which comprises providing a platelet enriched solution including an effective amount of anti-oxidant such as ascorbic acid and an activator effective amount of a cofactor, e.g., a divalent cation cofactor; and activating the solution with an activator or agonist as described above.

Regardless of the amount of set up gelation time, the present invention includes an anti-oxidant that allows the gel to retain its viscosity for a longer duration. For example, ascorbic acid is believed to preserve the longevity of the gel viscosity. Another method of making the wound healing composition includes the steps of mixing activated growth factors with ascorbic acid. Said activated growth factors may be obtained in a variety of ways, such as by the steps of sequestering concentrated platelets from blood and mixing thrombin with said platelets. The ascorbic acid should be in sufficient amount to enhance the preservation of the gelatinous state of the final wound healing composition, and said thrombin should be in sufficient amount to facilitate formation of the coagulum (gel) having the desired level of viscosity while sufficiently activating growth factors present in the composition and the wound.

In one preferred version of the composition, ascorbic acid (for instance, a 1 ml of a Cenolate® ascorbic acid solution (500 mg/ml; Abbott Laboratories, Inc., North Chicago, Ill., USA)) is admixed with about 5 cc and 10 cc, preferably about 8 cc of concentrated platelets, then about 500 U and about 10,000 U, preferably about 1000 U of calcified thrombin (prepared by the addition of 1 cc of 10% $CaCl_2$/ 1000 U of thrombin solution) is admixed into the platelet-lascorbic acid admixture. However, other ratios of concentrated platelets:ascorbic acid:thrornbin may be useful, depending upon the desired amount of healing agents, gelation time, gel viscosity and longevity. The method of making a wound healant may further include, prior to or contemporaneous with mixing said thrombin, mixing at least one of the aforementioned vitamins in sufficient amount(s) to further enhance wound healing. Alternatively, said method may include, prior to or contemporaneous with mixing said thrombin, mixing at least one of the aforementioned antibiotics in sufficient amount(s) to reduce infection by bacteria.

Besides a method of making a wound healant composition, the invention described herein may also include a method of treating a wound, comprising the steps of applying a sufficient amount of a composition of matter comprising growth factors and ascorbic acid to enhance healing of the wound. Said method of treating a wound may include the use of any of the compositions described herein; it may also include the use of any composition made by any of the methods described herein.

Once applied to a wound, the composition may remain on the wound for as long as 5 days, and perhaps longer depending upon the circumstances such as the location of the wound and other wound characteristics. Although the composition and method described herein are especially useful for the treatment of chronic wounds, they may also be useful in the treatment of acute wounds.

EXAMPLE 1

Preparation of Platelet Enriched Wound Healant (a) Whole Blood Method

One manner of making the plasma-poor concentrated platelets of the present invention is to collect about 450 ml of whole blood in anticoagulant (such as sodium citrate or any similar anticoagulant known in the field). That blood is then centrifuged in a MCS® Plus LN-9000 centrifuge (Haemonetics, inc.) using an LN 994 disposable collection kit (Haemonetics, Inc.) at about 2,400 rpms for a duration of about 20 minutes to separate out a band of: (a) plasma and most white blood cells; (b) platelets (and incidental white blood cells); and (c) red blood cells. The platelet portion is then re-centrifuged to further separate out plasma (and incidental white blood cells) at 4,800 rpms for a duration of about 7½ minutes.

The final yield is about 45 ml of plasma-poor concentrated platelets (in trace or incidental amounts of residual plasma and white blood cells). Both the plasma/leukocyte portion and the red blood cell portion may be reinfused back into the patient. The concentration of the platelets fell within an acceptable platelet Concentration ranging between about 350,000 and about $2\times10^6$ cells/ml of platelet concentrate.

The plasma-poor concentrated platelets (8 ml) is then admixed with 1 ml of aqueous ascorbic acid solution (concentration 500 mg/ml; Cenolate® ascorbic acid injection, USP, available from Abbott Laboratories, North Chicago, Ill., USA) in a sterile vial. The platelet mixture is then activated by the addition of 1 ml of a 10% $CaCl_2$./1000 U thrombin (prepared by admixing 5 ml of aqueous 10% $CaCl_2$, (Calcium chloride injection, USP 10%, American Regent Laboratories, Inc., Shirley, N.Y., USA) with 5000 U Thrombin (Thrombogen® Thrombin, topical USP (bovine origin)), 5000 U, Johnson & Johnson Medical Inc., Arlington, Tex., USA).

Depending upon the relative concentrations of the ingredients, the resulting mixture may be either a liquid, or it may set up as a hard material or (preferably) as a gel having a viscosity dependant upon the relative amounts of thrombin and platelets; the relative concentrations of calcified thrombin to platelets determines how quickly the composition sets up, and how hard it will eventually be. Some mixtures will yield a composition that will set up in a gel in several seconds, whereas some mixtures will yield a composition that takes several minutes to set up in a gel.

(b) Platelet Method

This example illustrates another method of making the composition allows the extraction of blood, sequestering of plasma-poor concentrated platelets, mixing of additives and return of unused blood components to the patient, all in about 20 to 30 minutes and by making only one puncture in the patient. Approximately 125 to 250 ml of blood is extracted from a patient, with the blood drawing apparatus optionally remaining in place connected to the patient (for later use in returning unused blood components to the patient). That blood is transferred to a Lathum bowl and, using the same centrifuge described in above method (a), centrifuged at about 4,800 rpms until a band (or similar grouping) of plasma forms at the upper periphery (about 5 to 15 minutes), and a band (or similar grouping) of red blood cells forms at the bottom of the bowl; the center is comprised of plasma-poor concentrated platelets. The plasma band is removed for return to the patient, and the remaining blood components are again centrifuged at that speed (and sufficient duration), further removing plasma and white blood cells from the plasma-poor concentrated platelets. The plasma-poor concentrated platelets are then removed for mixing with the other additives described herein (thrombin, ascorbic acid and/or retinoids). See method (a) above.

EXAMPLE 2

Case Study

Case study: Patient P is a 57 year old white male truck driver with a right heel diabetic ulcer of 11 months' duration. His treatment regimen has consisted of rest, off-loading and daily wound cleansing with soap and water followed by application of gauze dressing. Carrasyn gel was ordered for a brief period, without improvement. Upon referral to an outpatient physical therapy department for wound treatment, P's current therapy consists of weekly sharp debridement, wet saline gauze and total contact cast. P has history of hypertension, which is controlled at present time. He has a 15-year history of diabetes mellitus with neuropathy, which is controlled with oral hypoglycemic elements.

P began treatment with the invention disclosed herein. After his wound was sharply debried, a gel coagulum prepared as described in Example 1 was applied and the wound was covered with a wet saline dressing. A total contact cast was then applied and left intact for one week. At the conclusion of week 1, the cast was removed, the wound site cleansed and recovered with wet dressing; the limb was re-cast for week 2. After the conclusion of week 2, the same procedure was followed, except that the gel coagulum was again applied to the wound site before covering with wet dressing.

After the conclusion of week 3 the same procedure as for week 2 was followed. This regimen continued for a total of 36 days. Table 1 below contains the data reflecting the reduction in wound site volume and surface area during weeks 1 through 4.

TABLE 1

| Week # | Volume (mm³) | Area (mm²) |
|---|---|---|
| 0 | 3121 | 674 |
| 1 | 1561 | 562 |
| 2 | 279 | 301 |
| 3 | 26 | 282 |
| 4 | 15 | 159 |

EXAMPLE 3

Case Study

In this Example, five patients that entered into this study were referrals by their physicians. The patients were then screened using the exclusion, inclusion criteria. The patients selected for study had an ulcer of the lower extremity that had not healed after four to six months of treatment either with traditional wound care alone, or with traditional care plus Regranex[1].

[1] A single growth factor product of Ortho-McNeal marketed by Johnson & Johnson.

All five of the study patients had a platelet count of 100,000 cells/mm³ or greater, and had a hemoglobin >10 g and a HCT of 30% or greater. The patients were evaluated for infection in the wound, and for osteomyelitis. None of the patient studied showed signs of infection, or bone involvement.

Aggressive debridement to essentially change the chronic wound to an acute one was used. The ulcer and surrounding callus were completely excised down to normal uninvolved tissue. All subjects were treated as outpatients. All patients agreed to be totally non-weight-bearing. With the exception of one, patients were supplied with a half-shoe that transferred weight to the unaffected area of the foot. The one patient not fitted with the half-shoe was fitted with a full case of the lower leg. Direct questioning of patients and family assessed the compliance issue. Only one patient proved to be non-compliant. Patient 4's blood sugar exceeded 400 mg/dl and she became disoriented and walked on her foot as post treatment day 2. This resulted in a re-treatment of patient 4[2]. Table 2 shows the wound size and volume at the commencement and conclusion of treatment with the gel coagulum disclosed herein (Example 1). Closure, on the average, took less than four weeks. The average wound was brought to 99% closure in 25 days.

[2] Pt#4 NG was non-compliant through out this study, missing three clinic visits.

TABLE 2

| | Volume (mm³) | | Area (mm²) | |
|---|---|---|---|---|
| Pt # | Start | End | Start | End |
| 1 | 3121 mm³ | 15 mm³ | 674 mm² | 159 mm² |
| 2 | 358 mm³ | 0.0 mm³ | 65 mm² | 4 mm² |
| 3 | 293 mm³ | 3.0 mm³ | 63 mm² | 3 mm² |
| 4 | 192 mm³ | 18 mm³ | 104 mm² | 39 mm² |
| 5 | 336 mm³ | 0.0 mm³ | 181 mm² | 0.0 mm² |

EXAMPLE 4

Expanded Clinical Case Study

In this Example, the gel composition prepared in accordance with Example 1 was evaluated in 62 patients with a variety of chronic wound types resulting from several causes, including diabetic complications, trauma including wounds resulting from surgical or medical procedures, pressure (decubitus sores), and spider bites. The patients were divided into four (4) clinical groups, and were all categorized according to wound duration, wound type, date of treatment initiation and starting wound volume, extent of wound closure and time duration to reach wound closure. The results are tabulated in Table 3 below and are summarized graphically in FIG. 1.

FIG. 1 is an illustration summarizing the levels of response for all 62 patients with various wound types following treatment with the gel coagulum of the invention. The results show that 46.8% of all patients had 100% closure after receiving, on average, 2.24 treatments over an averaged time duration of 8.74 weeks. The breakdown of the results according to wound types is shown in Table 5 below.

TABLE 3

| Wound Type | No. Successful patients[a]/ No. total patients | % Wound closure[b] |
|---|---|---|
| Diabetic | 25/29 | 86 |
| Venous | 7/15 | 47 |

TABLE 3-continued

| Wound Type | No. Successful patients[a]/ No. total patients | % Wound closure[b] |
|---|---|---|
| Pressure | 3/5 | 60 |
| Trauma | 5/8 | 63 |
| Spider | 2/2 | 100 |

[a]Patients with over 90% wound closure after treatment with gel coagulum.
[b]Percent of patients with over 90% wound closure of a specific wound type after treatment with gel coagulum relative to all patients with the same wound type.

| ID | Wound Duration | Wound Type | 1st TX Date | Initial Wound Vol. | Current Wound Vol. | # of TX's | % Closure | Date | Week's to Healing. or Current Closure |
|---|---|---|---|---|---|---|---|---|---|
| | | | | BENNETT WOUND THERAPY | | | | | |
| Mcla | 12 months | Diabetic | Aug. 2, 1999 | 853 mm³ | 0 | 2 | 100% | Aug. 30, 1999 | 4 |
| Rcoo | 1 month | Venous | Sep. 8, 1999 | 2660 mm³ | 0 | 1 | 100% | Oct. 8, 1999 | 4.5 |
| Sdlc | 12 months | Diabetic | Oct. 1, 1999 | 586 mm³ | 0 | 2 | 100% | ###### | 6.5 |
| Mdrl | 48 months | Diabetic | Feb. 22, 2000 | 22811 mm³ | 0 | 1 | 100% | Apr. 25, 2000 | 9 |
| Near | NA | Surgical | Dec. 20, 1999 | 583625 mm³ | 0 | 1 | 100% | Mar. 6, 2000 | 11 |
| Rfau | 1 month | Venous | Oct. 20, 1999 | 600 mm³ | 0 | 2 | 100% | ###### | 8 |
| Dgra | 2 months | Diabetic | Sep. 8, 1999 | 160 mm³ | 0 | 3 | 100% | Jan. 11, 2000 | 18 |
| Jhor | 1 month | Diabetic | Oct. 19, 1999 | 286 mm³ | 0 | 4 | 100% | Jan. 11, 2000 | 12 |
| Ajoh | 288 mo. (24 yrs) | Venous | Aug. 9, 1999 | 1600 mm³ | 0 | 4 | 100% | ###### | 10 |
| Djoh | <1 month | Burn | Sep. 22, 1999 | 2761 mm³ | 0 | 1 | 100% | ###### | 3 |
| Plal | 1 month | Diabetic | Oct. 8, 1999 | 264 mm³ | 0 | 1 | 100% | ###### | 7.5 |
| Amcc | 2 months | Diabetic | Jan. 13, 2000 | 1700 mm³ | 0 | 1 | 100% | Apr. 4, 2000 | 11.5 |
| Dvil | <1 month | Diabetic | Jan. 17, 2000 | 933 mm³ | 0 | 3 | 100% | Mar. 29, 2000 | 10 |
| Pwhl | 1 month | Diabetic | Oct. 13, 1999 | 1000 mm³ | 0 | 1 | 100% | ###### | 5 |
| Cwho | 2 months | Spider | Jul. 7, 1999 | 18676 mm³ | 0 | 2 | 100% | ###### | 14 |
| Myat | 1 month | Diabetic | Sep. 23, 1999 | 595 mm³ | 0 | 3 | 100% | Jan. 24, 2000 | 17 |
| Jbea | 180 mo. (15 yrs) | Diabetic | Mar. 14, 2000 | 440 mm³ | 102 mm³ | 7 | 77% | Jun. 21, 2000 | 14 |
| Dbru | 1.5 months | Surgical | May 2, 2000 | 164749 mm³ | 56028 mm³ | 1 | 66% | May 16, 2000 | 2 |
| Wbur | NA | Diabetic | Mar. 29, 2000 | 32099 mm³ | 580 mm³ | 6 | 98% | Jun. 8, 2000 | 10 |
| Mbye | 4 months | Diabetic | Jan. 11, 2000 | 3001 mm³ | 0 | 5 | 100% | May 16, 2000 | 18 |
| Ccan | 2 months | Pressure | Apr. 20, 2000 | 800 mm³ | 0 | 4 | 100% | Jun. 22, 2000 | 9 |
| Bcla | 1 month | Spider | Apr. 25, 2000 | 14007 mm³ | 0 | 2 | 100% | Jun. 20, 2000 | 8.5 |
| Ccle | 3 months | Decubitus | Feb. 24, 2000 | 1900 mm³ | 3169 mm³ | 7 | 0 | Jun. 8, 2000 | 15 |
| Wcot | 18 months | Venous | Apr. 25, 2000 | 2701 mm³ | 583 mm³ | 3 | 78% | Jun. 1, 2000 | 5 |
| Ffer | 8 months | Diabetic | Feb. 7, 2000 | 4168 mm³ | 160 mm³ | 6 | 96% | Jun. 22, 2000 | 19.5 |
| Dshe | 10 months | Diabetic | Apr. 20, 2000 | 12272 mm³ | 1248 mm³ | 4 | 90% | Jun. 22, 2000 | 9 |
| Jshe | 3 months | Diabetic | May 16, 2000 | 144 mm³ | 17 mm³ | 2 | 88% | Jun. 6, 2000 | 3 |
| Wsme | 14 months | Diabetic | Aug. 4, 1999 | 2667 mm³ | 5 mm³ | 2 | 99% | Jun. 13, 2000 | 45 |
| Lsmi | 8 months | Diabetic | Feb. 15, 2000 | 128 mm³ | 0 | 7 | 100% | Jun. 20, 2000 | 18 |
| Wspu | 144 mo. (12 yrs) | Venous | Jun. 30, 1999 | 18009 mm³ | 666 mm³ | 22 | 96% | Jun. 21, 2000 | 51 |
| Fbla | 4 months | Diabetic | May 25, 2000 | 306 mm³ | 133 mm³ | 2 | 57% | Jun. 22, 2000 | 4 |
| Rwil | 9 months | Venous | Feb. 24, 2000 | 986 mm³ | 28 mm³ | 8 | 97% | Jun. 13, 2000 | 16 |
| Jwoo | 4 months | Club Foot | May 30, 2000 | 120 mm³ | 10 mm³ | 1 | 92% | Jun. 20, 2000 | 3 |
| | | | | CALDWELL | | | | | |
| Cwin | 3 months | Pressure | Mar. 16, 2000 | 273836 mm³ | 16008 mm³ | 7 | 94% | Jun. 6, 2000 | 11.5 |
| Jspe | 12 months | Venous | Jun. 8, 2000 | 28814 mm³ | 7803 mm³ | 1 | 73% | Jun. 13, 2000 | 1 |
| Jemm | 6 months | Diabetic | Mar. 30, 2000 | 933 mm³ | 27 mm³ | 3 | 97% | May 2, 2000 | 5 |
| Jker | NA | Pressure | Jun. 8, 2000 | 2251 mm³ | 1067 mm³ | 1 | 53% | Jun. 13, 2000 | |
| Rhow | 4 months | Pressure | Apr. 6, 2000 | 12006 mm³ | 0 | 2 | 100% | Jun. 14, 2000 | 10 |
| Mjon | 12 months | Diabetic | May 3, 2000 | 1600 mm³ | 373 mm³ | 3 | 77% | Jun. 15, 2000 | 6 |
| | | | | HSM-METH | | | | | |
| Wenn | 105 mo. (9 yrs) | Arterial | May 8, 2000 | 14967 mm³ | 14791 mm³ | 1 | 0.01% | May 16, 2000 | 1 |
| Bbou | 4 months | Trauma | May 2, 2000 | 13147 mm³ | 520 mm³ | 4 | 96% | Jun. 19, 2000 | 7 |
| Bbou | 4 months | Trauma | May 2, 2000 | 598 mm³ | 0 mm³ | 3 | 100% | Jun. 1, 2000 | 4 |

-continued

| ID | Wound Duration | Wound Type | 1st TX Date | Initial Wound Vol. | Current Wound Vol. | # of TX's | % Closure | Date | Week's to Healing. or Current Closure |
|---|---|---|---|---|---|---|---|---|---|
| Gger | Est. 20 years | Venous | Apr. 27, 2000 | 8590 mm$^3$ | 1920 mm$^3$ | 2 | 78% | Jun. 12, 200 | 7 |
| Gger | Est. 20 years | Venous | Apr. 27, 2000 | 793 mm$^3$ | 659 mm$^3$ | 2 | 17% | Jun. 12, 2000 | 7 |
| Gger | Est. 20 years | Venous | Apr. 27, 2000 | 815 mm$^3$ | 1073 mm$^3$ | 2 | 0% | Jun. 12, 2000 | 7 |
| Kcar | 6 months | Diabetic | Apr. 26, 2000 | 640 mm$^3$ | 47 mm$^3$ | 3 | 93% | Jun. 7, 2000 | 6 |
| Vols | 6 months | Trauma | Apr. 27, 2000 | 2534 mm$^3$ | .667 mm$^3$ | 2 | 99% | Jun. 26, 2000 | 9 |
| Mjos | 193 mo. (16 yrs) | Venous | Apr. 26, 2000 | 1664 mm$^3$ | 3241 mm$^3$ | 3 | 0% | Jun. 12, 2000 | 7 |
| Baug | NA | Trauma | Jun. 15, 2000 | 1814 mm$^3$ | 400 mm$^3$ | 1 | 78% | Jun. 19, 2000 | 4 days |
| Alev | NA | Venous | May 23, 2000 | 2977 mm$^3$ | 1323 mm$^3$ | 2 | 56% | Jun. 15, 2000 | 3 |
| Mmad | 18 months | Venous | May 4, 2000 | 1000 mm$^3$ | 469 mm$^3$ | 3 | 53% | Jun. 8, 2000 | 4 |
| Cdic | NA | Trauma | Apr. 27, 2000 | 2871 mm$^3$ | 2401 mm$^3$ LRCF | 2 | 16% | Jun. 8, 2000 | 5 |
| Rail | 36 mo. (3 yrs) | Diabetic | Nov. 13, 1999 | 2941 mm$^3$ | 0 | 1 | 100% | Dec. 8, 1999 | 3 |
| Catk | 24 months | Diabetic | Mar. 1, 2000 | 13340 mm$^3$ | 27 mm$^3$ | 2 | 99% | May 3, 2000 | 8 |
| Rbak | 8 months | Diabetic | Feb. 11, 2000 | 133 mm$^3$ | 6 mm$^3$ | 1 | 95% | Mar. 2, 2000 | 3 |
| Habr | 4 months | Diabetic | Jul. 6, 1999 | 880 mm$^3$ | 0 | 1 | 100% | Aug. 12, 1999 | 5 |
| Bbol | 144 mo. (12 yrs) | Venous | Dec. 22, 1999 | 800 mm$^3$ | 0 | 3 | 100% | Mar. 6, 2000 | 10 |
| Jbri | 6 months | Diabetic | Dec. 1, 1999 | 32 mm$^3$ | 0 | 1 | 100% | Dec. 6, 1999 | 5 days |
| Fbri | 2 months | Venous | May 17, 2000 | 3601 mm$^3$ | 200 mm$^3$ | 1 | 94% | Jun. 21, 2000 | 4 |
| Shui | 5 months | Surgical | Apr. 18, 2000 | 1467 mm$^3$ | 0 | 2 | 100% | Jun. 7, 2000 | 7 |
| Rmar | 24 months | Diabetic | Mar. 29, 2000 | 21 mm$^3$ | 0 | 1 | 100% | Apr. 25, 2000 | 4 |
| Rmcd | 4 months | Diabetic | Dec. 31, 1999 | 4 mm$^3$ | 0 | 1 | 100% | Feb. 7, 2000 | 5 |

What is claimed is:

1. A method of treating a wound in a patient comprising the steps of applying to a wound a composition comprising a therapeutically effective amount of an activated platelet concentrate in combination with an effective gelation prolonging amount of ascorbic acid in an amount ranging between about 20 mg and about 65 mg/ml of platelet concentrate.

2. The method according to claim 1, wherein said activation of said platelets results from the inclusion of an agonist.

3. The method according to claim 2, wherein said agonist is selected from the group consisting of thrombin, collagen serotonin, ADP and acetylcholine (ACH), and combinations thereof.

4. The method according to claim 2, wherein said activation of said platelets results from the inclusion of thrombin.

5. The method according to claim 1, wherein said platelet concentrate is autologous.

6. The method according to claim 1, wherein said composition further comprises at least one retinoid.

7. The method according to claim 6, wherein said retinoid is vitamin A.

8. The method according to claim 1, wherein said composition further comprises vitamin E.

9. The method according to claim 2, wherein said composition further comprises at least one antibiotic.

10. The method according to claim 9, wherein said antibiotic is bacteriocidal to at least *Pseudomonas* and *Klebsella* bacteria.

11. The method according to claim 9, wherein said antibiotic is selected from the group consisting of a neosporin, vancomycin and gentamycin, and combinations thereof.

12. The method according to claim 1, wherein said wound healant composition further comprises at least one retinoid and at least one antibiotic which is bacteriocidal to *Pseudomonas* and *Klebsella* bacteria.

* * * * *